(12) United States Patent
Pierobon et al.

(10) Patent No.: US 11,408,896 B2
(45) Date of Patent: Aug. 9, 2022

(54) METHODS FOR DISCOVERING PROTEIN-PROTEIN INTERACTIONS

(71) Applicant: George Mason University, Fairfax, VA (US)

(72) Inventors: Mariaelena Pierobon, Fairfax, VA (US); Emanuel Petricoin, Fairfax, VA (US); Elisa Baldelli, Fairfax, VA (US)

(73) Assignee: George Mason University, Fairfax, VI (US)

( * ) Notice: Subject to any disclaimer, the term of this patent is extended or adjusted under 35 U.S.C. 154(b) by 0 days.

(21) Appl. No.: 16/445,938

(22) Filed: Jun. 19, 2019

(65) Prior Publication Data

US 2019/0383823 A1 Dec. 19, 2019

Related U.S. Application Data

(60) Provisional application No. 62/686,868, filed on Jun. 19, 2018.

(51) Int. Cl.
| | | |
|---|---|---|
| *G01N 31/00* | (2006.01) | |
| *G01N 33/53* | (2006.01) | |
| *G01N 33/68* | (2006.01) | |
| *G01N 33/50* | (2006.01) | |

(52) U.S. Cl.
CPC ..... *G01N 33/6845* (2013.01); *G01N 33/5044* (2013.01); *G01N 2333/71* (2013.01); *G01N 2800/7028* (2013.01)

(58) Field of Classification Search
None
See application file for complete search history.

(56) References Cited

PUBLICATIONS

Zhang et al. (Molecular & Cellular Proteomics, 16:10, pp. 891-910, 2017) (Year: 2017).*
Ummanni et al. (Biochimica Biophysica Acta, vol. 1844, 2014, pp. 950-959) (Year: 2014).*
Moerke et al. (Curr Protoc Chern Biol.; 8(3): 179-196, 2017) (Year: 2017).*

* cited by examiner

*Primary Examiner* — Lisa V Cook
(74) *Attorney, Agent, or Firm* — Dave Law Group LLC; Raj S. Dave

(57) ABSTRACT

An embodiment relates to a method, comprising: obtaining a biological sample, performing a protein complex immunoprecipitation (Co-IP) on the sample, performing a reverse phase protein array (RPPA) on the sample after performing the protein complex immunoprecipitation, and identifying one or more protein complexes. A further embodiment relates to a method of treatment, comprising: obtaining a tissue sample from a patient, performing Co-IP then RPPA on the sample, identifying a protein complex, determining whether the protein complex comprises known protein drug targets, and treating the patient with a drug that interacts with the known protein drug targets.

20 Claims, No Drawings

METHODS FOR DISCOVERING PROTEIN-PROTEIN INTERACTIONS

CROSS-REFERENCE TO RELATED APPLICATIONS

This application claims the benefit under 35 U.S.C § 119 of U.S. Provisional Application No. 62/686,868, filed Jun. 19, 2018, which is hereby incorporated by reference in its entirety.

FIELD OF THE INVENTION

This invention relates to the process of identifying protein-protein interactions (PPI) in any cell type, using a method that is high-throughput, has high sensitivity, and can concomitantly capture hundreds of PPI. The invention is more particularly concerned with a process involving isolation of protein complexes using conventional Co-immunoprecipitation (Co-IP) coupled with Reverse Phase Protein Array (RPPA).

BACKGROUND OF INVENTION

An embodiment relates to identifying one or more protein complexes by obtaining a sample, performing protein complex immunoprecipitation (Co-IP) on the sample, and performing reverse phase protein array (RPPA) on the sample after Co-IP.

Currently, protein-protein interactions (PPI) are explored using different platforms, which have been developed over the years, including mass spectrometry-based analyses, sandwich immunoassay, microarrays, proximity ligation assays, hybrid assays, fluorescent imaging-based biophysical techniques, etc. Exploration of PPI often requires upfront sample purification (e.g. Co-IP, affinity tags for tandem affinity purification, protein-fragment complementation, etc), which is labor-intensive and not conducive to high-throughput.

Although genetic alterations play a central role in tumor development, alternated protein networks are the real engine that drive cellular biology and determine response to treatment. Consequently, proteins are the direct targets of the vast majority of targeted drugs. Because proteins do not act in isolation, cellular functions (e.g. cell growth, differentiation, motility, death, and dissemination) depend upon dynamic and hierarchically regulated protein interactions and formation of heterogeneous protein complexes.

De-novo elucidation of PPI often uses mass spectrometry as a read out method to identify members of these protein complexes. However, mass spectrometry requires millions to billions of cells as input, rendering the approach highly challenging when using clinical tissue samples, where cellular amounts are in the hundreds to thousands of cells.

As described herein, we have invented a novel method using a protein array tool for de-novo identification of PPI in any cell type, for exploring intracellular communication systems, and for identifying new therapeutic targets. While protein-protein interactions (PPI) have previously been studied using many methods, the method we describe is superior to others in terms of: 1) sensitivity; 2) high throughput, with hundreds of samples simultaneously analyzed; 3) multiplexing, with hundreds of interactions concomitantly captured, 4) requirement for very small numbers of cells, and 5) the use of serial Co-IPs to isolate different members of any given pathway for comprehensive PPI and signaling profiling. Our method includes isolation of protein complexes using conventional Co-immunoprecipitation (Co-IP) coupled with Reverse Phase Protein Microarray for the down-stream identification of proteins that are physically interacting. This method allows the capture of functional PPI and provides qualitative, quantitative, and kinetic read-out of these interactions. We call this new method Multinodal Protein Interactome Network Array (MPINA). Co-IP methods that can be used for MPINA include, but are not limited to, antibodies, DARPins, as well as other sample enrichment methods.

The present invention has been tested on in vitro models and optimized for analysis of human samples. Although the invention has been tested on tumor samples as proof of concept, it can be used to explore protein networks in any cell type and disease.

The "Multinodal Protein Interactome Network Array" is a unique assay as it combines serial Co-IPs of proteins contained within a specific signaling network with a high-throughput, multiplex read-out via RPPA. Co-IPs are used to isolate different nodes within or across pathways; the RPPA is used to measure the expression and activation level of the members of these protein complexes using antibodies targeting the phosphorylated site of the protein of interest. The use of the protein array technology allows for an unprecedented, high volume number of activated proteins in these networks and generates high-throughput, multiplex data starting from a relatively small amount of input material.

This methodology can be used to explore the role of PPI in disease onset and progression as well as to identify protein signaling complexes associated with response to targeted treatments. Specific predictive or prognostic interactions may be used to develop commercially available tests to guide treatment selection. This platform can also be used as a novel tool in the drug discovery process.

SUMMARY OF INVENTION

An embodiment relates to a method, comprising: obtaining a sample, performing a protein complex immunoprecipitation on the sample, performing a reverse phase protein array on the sample after performing the protein complex immunoprecipitation, and identifying a protein complex.

In one embodiment identifying a protein complex further comprises identifying activated members of the protein complex In another embodiment the activated members of the protein complex include proteins that are phosphorylated, acylated, alkylated, hydroxylated, glycosylated, cleaved, iodinated, succinylated, amidated, myristoylated, farnysilated, and/or palmitoylated.

In an embodiment the sample comprises a cell lysate, mammalian cells, or tumor cells. The method of claim 4, wherein the tumor cells are KRAS mutant cells from non-small cell lung cancer (NSCLC).

In another embodiment the sample comprises cells obtained from a tissue or a cell line.

In one embodiment the method further comprises treating the sample with an agent prior to the performing the protein complex immunoprecipitation In another embodiment the method further comprises immunoprecipitating the sample with one or more antibodies after treating the sample with the agent.

In one embodiment performing the protein complex immunoprecipitation comprises carrying out the protein complex immunoprecipitation in a serial mode with more than one antibody.

In one embodiment performing the protein complex immunoprecipitation comprises immunoprecipitating protein complexes including EGFR, RAS, ERK, CREB, STAT, and/or AKT.

In one embodiment performing the reverse phase protein array comprises using a robotic printing platform In another embodiment the method further comprises making a comparison with a control lysate sample.

In one embodiment the method further comprises identifying activated members of protein complexes of one or more of EGFR, RAS, ERK, CREB, STAT, and/or AKT-mTOR pathways.

In one embodiment the protein complex comprises a protein signaling complex.

An embodiment relates to a method of treatment, comprising: obtaining a tissue sample from a patient, performing a protein complex immunoprecipitation on the sample, performing a reverse phase protein array on the sample after performing the protein complex immunoprecipitation, identifying a protein complex, determining whether the protein complex comprises known protein drug targets, and treating the patient with a drug that interacts with the known protein drug targets.

In one embodiment the known protein drug targets are physically associating with other proteins known to transduce cellular signals.

In one embodiment the drug disrupts kinase activity or protein-protein interactions.

In another embodiment the tissue sample is derived from isolating diseased cells of the patient from cells including tumor cells, blood cells, fat cells, liver cells, and nerve cells.

In one embodiment the method further comprises treating the patient with therapeutic agents.

In another embodiment the method further comprises monitoring a response of the patient to the treating the patient with a drug that interacts with the known protein drug targets.

DETAILED DESCRIPTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

Embodiments relate to the development and validation of a protein array based approach to assess protein-protein interactions (PPI) and protein complex formation within cellular signaling networks. The technique combines the power of Reverse Phase Protein Microarray (RPPA) with Co-immunoprecipitation (Co-IP) techniques and allows exploration in a highly multiplexed format PPI display of functional interactions and characterization of these interactions from a qualitative, quantitative, and kinetic standpoint. The method has been optimized in several aspects, including lysing conditions, amount of cross-linker needed for better preservation of the complexes during the procedure, antibody to protein ratio for the Co-IP, and sample requirement for the RPPA.

The methods and techniques of the present invention are generally performed according to conventional methods well known in the art and as described in various general and more specific references, such as Baldelli et al. Methods Mol Biol. 2017; 1606:149-169 and Smith A L et al PLoS One. 2011 20; 6(1):e16206., that are cited and discussed throughout the present specification unless otherwise indicated. The nomenclatures used in connection with, and the procedures and techniques of molecular biology, cell biology, proteomics, biochemistry, and other related fields described herein are those well-known and commonly used in the art.

The following terms and phrases, unless otherwise indicated, shall be understood to have the following meanings.

The term PPI as used herein refers to protein-protein interactions.

The term RPPA as used herein refers to Reverse Phase Protein Array.

The term Co-IP as used herein refers to Co-immunoprecipitation.

The term MPINA as used herein refers to Multinodal Protein Interactome Network Array.

The term DARPin as used herein refers to designed ankyrin repeat protein.

The term RAS as used herein refers to Rat Sarcoma.

The term KRAS as used herein refers to Kirsten Rat Sarcoma virus.

The term NSCLC as used herein refers to Non-Small Cell Lung Cancer.

The term EFG as used herein refers to Epidermal Growth Factor.

The term EFGR as used herein refers to Epidermal Growth Factor Receptor.

The term ERK as used herein refers to extracellular signal-regulated kinases.

The term CREB as used herein refers to cAMP response element-binding protein.

The term STAT as used herein refers to members of the Signal Transducer and Activator of Transcription protein family.

The term AKT as used herein refers to the synonymous Protein kinase B (PKB).

The term m-TOR as used herein refers to the mechanistic target of rapamycin.

The phrase activated members of a protein complex as used herein refers to proteins that have been covalently modified, such that the proteins can perform biological functions, including being enzymatically in use. Such protein members can be covalently modified by being phosphorylated, acylated, alkylated, hydroxylated, glycosylated, cleaved, iodinated, succinylated, amidated, myristoylated, farnysilated, palmitoylated, etc.

The term drug as used herein refers to a man-made or natural molecule that exerts a biochemical or physiological effect on a cell, tissue, organ, or organism by physically or chemically interacting with one or more proteins.

The phrase drug target as used herein refers to one or more proteins with which a drug physically or chemically interacts.

The phrase therapeutic agent as used herein refers to one or more molecules that are administered to a patient to treat a disease or disorder.

The phrase transduce cellular signals as used herein refers to the process whereby a chemical or physical signal is transmitted through a cell as a series of molecular events, most commonly protein phosphorylation catalyzed by protein kinases, which ultimately results in a cellular response.

The phrase kinase activity as used herein refers to the ability of a protein to catalyze the transfer of phosphate groups from high-energy, phosphate-donating molecules to specific substrates, such as other proteins.

An embodiment makes it possible to identify one or more protein complexes by obtaining a sample, performing a protein complex immunoprecipitation on the sample, performing a reverse phase protein array on the sample after performing the protein complex immunoprecipitation, and identifying a protein complex.

In a variation of the embodiment identifying a protein complex further comprises identifying activated members of the protein complex In another variation of the embodiment the activated members of the protein complex include proteins that are phosphorylated, acylated, alkylated, hydroxylated, glycosylated, cleaved, iodinated, succinylated, amidated, myristoylated, farnysilated, and/or palmitoylated.

In a variation of the embodiment the sample comprises a cell lysate, mammalian cells, or tumor cells. The method of claim 4, wherein the tumor cells are KRAS mutant cells from non-small cell lung cancer (NSCLC).

In another variation of the embodiment the sample comprises cells obtained from a tissue or a cell line.

In a variation of the embodiment the method further comprises treating the sample with an agent prior to the performing the protein complex immunoprecipitation In another variation of the embodiment the method further comprises immunoprecipitating the sample with one or more antibodies after treating the sample with the agent.

In one variation of the embodiment performing the protein complex immunoprecipitation comprises carrying out the protein complex immunoprecipitation in a serial mode with more than one antibody.

In one variation of the embodiment performing the protein complex immunoprecipitation comprises immunoprecipitating protein complexes including EGFR, RAS, ERK, CREB, STAT, and/or AKT.

Epidermal growth factor receptor (EGFR) is a transmembrane protein that is activated by binding of its specific ligands, including epidermal growth factor and transforming growth factor α (TGFα) ErbB2 has no known direct activating ligand, and may be in an activated state constitutively or become active upon heterodimerization with other family members such as EGFR. Upon activation by its growth factor ligands, EGFR undergoes a transition from an inactive monomeric form to an active homodimer. In addition to forming homodimers after ligand binding, EGFR may pair with another member of the ErbB receptor family, such as ErbB2/Her2/neu, to create an activated heterodimer.

The epidermal growth factor receptor (EGFR; ErbB-1; HER1 in humans) is a transmembrane protein that is a receptor for members of the epidermal growth factor family (EGF family) of extracellular protein ligands. Human EGF is a 6-kDa protein with 53 amino acid residues and three intramolecular disulfide bonds. EGF binds to the epidermal growth factor receptor.

The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). In many cancer types, mutations affecting EGFR expression or activity could result in cancer.

The EGFR co-IP, for example, will allows identification of patients where activation of the drug target (in this case the EGFR receptor) is associated with the formation of a protein complex driven by protein-protein interactions that are responsible for the initiation of EGFR signal transduction.

RAS is a family of related proteins which is expressed in all animal cell lineages and organs. RAS protein family members belong to a class of protein called small GTPase, and are involved in transmitting signals within cells (cellular signal transduction). The 3 RAS genes in humans (HRAS, KRAS, and NRAS) are the most common oncogenes in human cancer; mutations that permanently activate RAS are found in 20% to 25% of all human tumors and up to 90% in certain types of cancer (e.g., pancreatic cancer).

Extracellular signal-regulated kinases (ERKs) or classical MAP kinases are widely expressed protein kinase intracellular signaling molecules that are involved in functions including the regulation of meiosis, mitosis, and postmitotic functions in differentiated cells.

CREB belongs to a superfamily of transcription factors that form homo- and heterodimers through a series of leucine residues and bind to specific DNA sequences. Within this superfamily, CREB and the closely related factors CREM (cAMP response element modulator) and ATF-1 (activating transcription factor-1) comprise a subcategory referred to as the CREB family. CREB-TF (CREB, cAMP response element-binding protein) is a cellular transcription factor. It binds to certain DNA sequences called cAMP response elements (CRE), thereby increasing or decreasing the transcription of the genes. CREB is a cAMP-responsive transcription factor regulating the somatostatin gene.

Members of the signal transducer and activator of transcription (STAT) protein family are intracellular transcription factors that mediate many aspects of cellular immunity, proliferation, apoptosis and differentiation. They are primarily activated by membrane receptor-associated Janus kinases (JAK).

Protein kinase B (PKB), also known as AKT, is a serine/threonine-specific protein kinase that plays a key role in multiple cellular processes such as glucose metabolism, apoptosis, cell proliferation, transcription and cell migration. AKT (Protein kinase B, PKB) is a serine/threonine kinase that plays a key in regulating cell survival, angiogenesis and tumor formation. AKT is a downstream mediator of the PI 3-K pathway, which results in the recruitment of AKT to the plasma membrane.

In one variation of the embodiment performing the reverse phase protein array comprises using a robotic printing platform.

In another variation of the embodiment the method further comprises making a comparison with a control lysate sample.

In one variation of the embodiment the method further comprises identifying activated members of protein complexes of one or more of EGFR, RAS, ERK, CREB, STAT, and/or AKT-mTOR pathways.

In one variation of the embodiment the protein complex comprises a protein signaling complex.

An embodiment makes it possible to treat a patient by obtaining a tissue sample from a patient, performing a protein complex immunoprecipitation on the sample, performing a reverse phase protein array on the sample after performing the protein complex immunoprecipitation, identifying a protein complex, determining whether the protein complex comprises known protein drug targets, and treating the patient with a drug that interacts with the known protein drug targets.

In one variation of the embodiment the known protein drug targets are physically associating with other proteins known to transduce cellular signals.

In one variation of the embodiment the drug disrupts kinase activity or protein-protein interactions.

In another variation of the embodiment the tissue sample is derived from isolating diseased cells of the patient from cells including tumor cells, blood cells, fat cells, liver cells, and nerve cells.

In one variation of the embodiment the method further comprises treating the patient with therapeutic agents.

In another variation of the embodiment the method further comprises monitoring a response of the patient to the treating the patient with a drug that interacts with the known protein drug targets.

The disclosed embodiments change the way in which protein-protein interactions (PPI) are identified in any cell type.

Example 1

To validate Multinodal Protein Interactome Network Array (MPINA) using KRAS mutant and wild-type Non-Small Cell Lung Cancer (NSCLC) cell lines and to demonstrate the ability of the MPINA to capture the qualitative, quantitative, and kinetic nature of these protein-protein interactions (PPI), cell lines were treated with Epidermal Growth Factor (EGF) for 5 min. Data presented herein were generated using two cell lines the A549 harboring a KRAS mutation, and the H1563 wild-type for the EGFR/KRAS genes. Protein complexes were isolated using antibodies (Co-IP) targeting EGFR, RAS, ERK, CREB, and AKT. Each Co-IP was then processed using the RPPA, where samples were probed with ~50 antibodies targeting phosphoproteins involved in the EGFR/KRAS signaling network. MPINA was also tested using human NSCLC specimens with KRAS mutation, EGFR L858R mutation, EGFR deletion at the exon 19, and KRAS/EGFR wild-type.

As shown in Table 1, different activated protein complexes were identified within the EGFR/RAS/ERK and the AKT-mTOR pathways in KRAS mutant and wild-type samples.

TABLE 1

Identification of activated protein complexes within the EGFR/RAS/ERK and the AKT-mTOR pathways in KRAS mutant and wild-type samples

| Antibody | EGFR Co-IP Ratio EGF stimulated/ unstimulated cells | | RAS Co-IP Ratio EGF stimulated/ unstimulated cells | | ERK Co-IP Ratio EGF stimulated/ unstimulated cells | | AKT Co-IP Ratio EGF stimulated/ unstimulated cells | | CREB Co-IP Ratio EGF stimulated/ unstimulated cells | |
|---|---|---|---|---|---|---|---|---|---|---|
| | H1563 cells | A549 cells | H1563 cells | A549 cells | H1563 cells | A549 cells | H1563 cells | A549 cells | H1563 cells | A549 cells |
| EGFR | 1.52 | 1.29 | 1.23 | 1.30 | 2.08 | 0.76 | 2.91 | 1.07 | 1.38 | 1.30 |
| EGFR Y1068 | 86.86 | 149.62 | 1.47 | 1.49 | 1.33 | 1.06 | 2.11 | 1.43 | 1.25 | 1.26 |
| EGFR Y1173 | 10.84 | 10.72 | 0.79 | 0.89 | 1.25 | 0.73 | 3.09 | 1.15 | 1.40 | 1.36 |
| ErbB2/HER2 Y1248 | 20.13 | 34.89 | 1.24 | 1.34 | 1.37 | 1.02 | 1.52 | 1.06 | 1.14 | 0.95 |
| ErbB3/HER3 Y1289 | 0.95 | 0.90 | 1.31 | 1.13 | 2.39 | 0.94 | 0.91 | 0.85 | 0.80 | 0.90 |
| IGF1R Y1131/IR Rec Y1146 | 1.15 | 1.09 | 1.47 | 1.01 | 1.06 | 0.92 | 2.36 | 0.96 | 0.84 | 1.13 |
| RSK3 T356/S360 | 1.00 | 1.09 | 1.43 | 1.37 | 1.56 | 1.25 | 3.80 | 1.08 | 0.76 | 1.08 |
| Shc Y317 | 11.29 | 17.69 | 1.17 | 1.30 | 1.67 | 1.20 | 2.62 | 1.49 | 0.86 | 1.07 |
| ERK 1/2 T202/Y204 | 3.25 | 3.92 | 3.28 | 2.94 | 3.14 | 3.69 | 7.20 | 1.61 | 2.08 | 1.49 |
| p90RSK S380 | 0.60 | 1.53 | 1.43 | 1.63 | 1.25 | 1.31 | 6.47 | 2.10 | 0.88 | 1.02 |
| CREB S133 | 0.97 | 1.12 | 1.31 | 1.11 | 1.63 | 0.97 | 1.28 | 0.93 | 2.56 | 1.86 |
| p38MAPK T180/Y182 | 0.79 | 0.93 | 1.88 | 1.32 | 2.26 | 1.13 | 1.78 | 0.85 | 0.83 | 0.91 |
| AKT S473 | 1.21 | 0.85 | 1.41 | 1.43 | 1.32 | 0.99 | 43.21 | 3.51 | 1.14 | 0.98 |
| AKT T308 | 0.49 | 0.80 | 1.01 | 0.88 | 1.48 | 0.92 | 7.02 | 1.35 | 1.95 | 0.84 |
| FKHR S256 | 0.36 | 0.59 | 1.03 | 1.17 | 2.16 | 1.79 | 1.35 | 0.76 | 1.48 | 0.88 |
| FKHR T24/FKHRL1 T32 | 0.46 | 0.77 | 1.05 | 0.90 | 2.48 | 1.20 | 1.59 | 0.70 | 2.36 | 0.67 |
| FKHRL1 S253 | 0.59 | 0.84 | 1.20 | 1.35 | 1.10 | 0.90 | 2.66 | 1.00 | 0.86 | 0.72 |
| GRB2 | 1.54 | 2.17 | 1.49 | 1.38 | 2.90 | 1.26 | 2.18 | 0.95 | 0.88 | 1.00 |
| GSK3a/b S21/9 | 0.83 | 0.79 | 1.32 | 1.39 | 2.25 | 1.09 | 2.39 | 1.01 | 0.95 | 1.00 |
| mTOR TOTAL | 0.89 | 0.80 | 1.35 | 1.36 | 2.27 | 1.13 | 1.38 | 0.97 | 0.78 | 0.82 |
| p70S6K T389 | 0.87 | 0.54 | 0.82 | 0.78 | 1.37 | 0.87 | 5.13 | 1.17 | 1.88 | 1.75 |
| p70S6K T412 | 0.46 | 1.11 | 1.38 | 1.82 | 1.51 | 1.22 | 4.23 | 2.22 | 0.83 | 1.06 |
| S6RP S240/244 | 0.88 | 0.82 | 1.63 | 1.53 | 2.05 | 3.97 | 2.22 | 0.56 | 0.76 | 0.91 |

TABLE 1-continued

Identification of activated protein complexes within the EGFR/RAS/ERK and the AKT-mTOR pathways in KRAS mutant and wild-type samples

| Antibody | EGFR Co-IP Ratio EGF stimulated/ unstimulated cells | | RAS Co-IP Ratio EGF stimulated/ unstimulated cells | | ERK Co-IP Ratio EGF stimulated/ unstimulated cells | | AKT Co-IP Ratio EGF stimulated/ unstimulated cells | | CREB Co-IP Ratio EGF stimulated/ unstimulated cells | |
|---|---|---|---|---|---|---|---|---|---|---|
| | H1563 cells | A549 cells | H1563 cells | A549 cells | H1563 cells | A549 cells | H1563 cells | A549 cells | H1563 cells | A549 cells |
| Histone H3 S10 | 0.67 | 0.80 | 1.49 | 1.53 | 2.00 | 0.91 | 1.22 | 0.91 | 0.66 | 0.93 |
| STAT1 Y701 | 0.95 | 0.78 | 1.02 | 1.09 | 1.09 | 0.79 | 2.03 | 1.26 | 0.80 | 1.11 |

Methods

The example relied on the use of the processes and materials described below.

Immunoprecipitation Protocol with Crosslinker
Solutions and Reagents:
PBS
DMSO
Tris-HCl 100 mM pH=7.4
Cross-linker solution: DSP (Thermo Scientific Cat #22585): Stock solution 50 mM in DMSO (8 mg DSP in 1 ml DMSO) diluted to 0.25 mM in PBS (Smith A L et al PLoS One. 2011 20; 6(1):e16206).
Quenching solution: L-Cystine 5 mM in Tris-HCl 20 mM pH=7.4. Dissolve 27 mg L-Cystine in Tris-HCl 100 mM; this solution is subsequently diluted 1:5 in PBS (Smith A L et al PLoS One. 2011 20; 6(1):e16206).
Lysis buffer: 915 µL Tissue Protein Extraction Reagent (T-PER, Pierce); 60 µL 5M Sodium Chloride; 10.0 µL 100 mM orthovanadate (Sigma Aldrich); 10.0 µL 200 mM PEFABLOC; 1.0 µL 5.0 mg/mL Aprotonin; 5.0 µL 1.0 mg/mL Pepstatin; and 1.0 µL 5.0 mg/mL Leupeptin.
EGF Receptor (EGFR1) Mouse mAb, Sepharose Bead Conjugate (Cell Signaling Cat #8083).
Akt (pan) (40D4) Mouse mAb, Sepharose Bead Conjugate (Cell Signaling Cat #3653).
Erk Mouse mAb (Cell Signaling Cat #9107).
RAS, clone RAS10 (Millipore Cat #05-516).
Anti-mouse IgG (H+L), F(ab')2 Fragment, Sepharose Bead Conjugate (Cell Signaling Cat #5946).
Extraction buffer: 1.0 mL Tissue Protein Extraction Reagent (T-PER, Pierce); 950 µL Novex® Tris-Glycine SDS Sample Buffer 2× (Invitrogen) supplemented with 50 µL 2-mercaptoethanol.
Cell line Lysate preparation
Remove media and rinse cells twice with PBS at room temperature.
Add 10 ml of cross-linker solution and incubate for 30 minutes at room temperature on a rocker/shaker.
Remove cross-linker solution and add 10 ml of quenching solution for 10 minutes at room temperature on a rocker/shaker.
Remove quenching solution and wash cells twice with ice-cold PBS.
Remove PBS and add 500 µl ice-cold lysis buffer to each flask (75 cm$^2$). Incubate the flask on ice for 5 minutes.
Scrape cells off the flask and transfer the lysate to a 2 ml microcentrifuge tube. Keep on ice.
Keep the lysates at 4° C. overnight to allow the debris to settle. Do not centrifuge the lysates.
Transfer the supernatant to a new tube.
Measure the protein concentration of the lysates. Any method with adequate sensitivity is used for measuring the protein concentration in samples prepared with lysis buffer. The Bradford Coomassie spectrophotometric method (Pierce) and a NanoDrop microvolume instrument (ThermoFisher) are adequate to measure protein concentration of lysed samples.
Adjust the protein concentration of the lysates to the final concentration of 1 mg/ml.
Immunoprecipitation with Sepharose Bead Conjugated Antibodies (Following Manufacturing Instructions)
Transfer 100 µl of lysate at 1 mg/ml to a new tube and add 5 µl of the bead conjugated primary antibody.
Incubate with gentle rocking for 2 hours at room temperature.
Centrifuge for 5 minutes at 14,000 g at 4° C.
Discard the supernatants and wash the pellets three times with 300 µl of Lysis buffer (1 min at 14000 g). Keep on ice during washes.
Resuspend the pellets in an adequate volume of extraction buffer (approximately 25 µl).
Boil samples for 8 minutes. Cool to room temperature.
Spin samples at 14,000 g and transfer the supernatants to a new tube.
Estimate final Co-IP samples protein concentration using the RPPA following the "Reverse Phase Protein Microarray Printing" and "Sypro Ruby Protein Blot Stain for Total Protein Determination" protocols listed below. Samples are printed onto nitrocellulose coated glass slides along with BSA standard curve ranging from 1 mg/ml to 0.125 mg/ml. Conventional interpolation methods can be used to estimate samples' concentration from the standard curve. Final sample concentration should be adjusted to 0.5 or 0.25 mg/ml. Samples should have similar protein concentration when printed on the array.
For long term storage, keep lysates at −80° C. until further processed. For short term storage, lysates can be kept at −20° C.
Immunoprecipitation with Non-Sepharose Bead Conjugated Antibodies (Following Manufacturing Instructions)
Transfer 100 µl of lysate at 1 mg/ml to a new tube and add 5 µl of Anti-mouse IgG (H+L), F(ab')2 Fragment.
Incubate with gentle rocking for 1 hour at 4° C.
Spin for 10 minutes at 10,000 g at 4° C. Transfer supernatants to a new tube.
Add 5 µl of primary antibody.
Incubate with gentle rocking for 2 hours at room temperature.

Add 5 µl of Anti-mouse IgG (H+L), F(ab')2 Fragment.
Incubate with gentle rocking for 1 hour at 4° C.
Centrifuge for 5 minutes at 14,000 g at 4° C.
Discard the supernatants and wash the pellets three times with 300 µl of Lysis buffer (1 min at 14000 g). Keep on ice during the washes.
Resuspend the pellet in an adequate volume of extraction buffer (approximately 8 µl).
Boil samples for 8 minutes and cool to room temperature.
Spin samples at 14,000 g and transfer supernatants to a new tube.
Estimate final Co-IP samples protein concentration using the RPPA following the "Reverse Phase Protein Microarray Printing" and "Sypro Ruby Protein Blot Stain for Total Protein Determination" protocols listed below. Samples are printed onto nitrocellulose coated glass slides along with BSA standard curve ranging from 1 mg/ml to 0.125 mg/ml. Conventional interpolation methods can be used to estimate samples' concentration from the standard curve. Final sample concentration should be adjusted to 0.5 or 0.25 mg/ml. Samples should have similar protein concentration when printed on the array.
For long term storage, keep lysates at −80° C. until further processed. For short term storage, lysates can be kept at −20° C.

Whole Tissue Lysates Preparation

Cut 8 µm sections from frozen tissue blocks and mount them on uncharged glass slides. (Six tissue sections are sufficient to pool down one protein).
Fix slides with 70% ethanol for a few seconds and rinse them in dH$_2$O. Let slides air dry. Add 50 µl of cross-linker solution on top of each section and incubate for 30 minutes at room temperature.
Remove cross-linker solution and add 50 µl of quenching solution on top of each section for 10 minutes at room temperature.
Remove quenching solution and wash each section twice with 500 µl ice-cold PBS.
Remove PBS and add 8 µl ice-cold lysis buffer to each section.
Scrape the tissue off the slide using a pipette tip or a scraper and collect the lysate on a screw-top tube. Keep the lysates on ice.
Adjust lysates volumes to 100 µl and keep them at 4° C. overnight to allow the cell debris to settle. Do not centrifuge the lysates.
Transfer the supernatant to a new tube.
Follow the Co-IP protocol listed above based on the type of antibody used (sepharose bead conjugated antibody versus non-sepharose bead conjugated antibody Reverse Phase Protein Microarray Printing The RPPA platform has been amply used for research studies and analysis of clinical samples since its invention. The following protocol is based on previously published SOPs (Baldelli et al. Methods Mol Biol. 2017; 1606:149-169). For the MPINA, printing process is performed using an Aushon 2470 arrayer equipped with twenty 185 µm pins. Control lysates (commercial cell lysates, recombinant peptides, or peptide mixtures that are known to contain the antigens being investigated) or standard curves are printed on the array along with experimental samples for internal quality control/quality assurance. Standard curves are used to directly correlate the signal measured in a given sample against a known standard using a curve-fitting model (e.g. linear fit, spline calibration models etc.). By using this approach, the absolute intensity values obtained from the RPPA analysis are transformed into relative units of the standard curve. Standard curves need to: 1) span the dynamic range of the analyte measured; 2) cover the dynamic range of the analyte within the linear range of the reference standard; and 3) contain constant amount of protein across all points of the curve while the concentration of the analyte of interest gradually decreases.

Equipment, Reagents and Materials:

Aushon 2470 arrayer (Aushon Biosystems) equipped with 185 µm diameter pins.
Nitrocellulose coated slides (ONCYTE® Nitrocellulose Film Slides, or Grace Bio-Labs);
384 well polystyrene microtiter plates (Genetix);
IP lysates;
Extraction buffer;
Desiccant (Drierite, anhydrous calcium sulfate);
Ziploc style plastic storage bags.

Sample Immobilization onto Nitrocellulose Coated Slides

Turn on the arrayer's power switch.
Fill the water wash container with dH$_2$O and empty the waste container. Care should be taken to verify tubing is sufficiently inserted into each container.
Fill the humidifier with dH$_2$O water.
Load nitrocellulose coated slides on platens with the nitrocellulose pad facing up and the label oriented to the right. If the IP lysates were frozen, thaw the lysates and heat the lysates for 2 minutes in a dry heat block or water bath at 100° C. Bring samples to room temperature and spin at 10,000×g for 15 sec.
Load samples into 384 well microplates.
Place a lid on each 384 well microplate.
Place each microplate on a plate.
Place the plate holder in the Aushon 2470 arrayer elevator with microplate well A1 facing the outside of the instrument. If samples are loaded in multiple plates, store the prepared plates in the arrayer with 60% humidity while pipetting samples in the remaining plates to limit sample evaporation.
Open the Aushon 2470 arrayer software.
Select the number of microplates by double clicking on "Genetix Polystyrene". Use the selected well plate grid to determine where samples are loaded into each plate. Click "Next".
Define the top offset as 4.5 mm and the left offset at 5.0 mm.
Set spot diameter to 250 µm.
Designate the feature-to-feature spacing in the X and Y-axis at 500 µm and 562.5 µm respectively.
To print triplicate spots on the vertical axis, select 2 replicates to be printed in a linear vertical position. This configuration allows the printing of 480 samples per superarray. Each replicate is printed from the same well of the 384 well plate.
Select 3 depositions per feature. Approximately 9 nL of lysate will be deposited on the nitrocellulose per spot.
Click "next" to set the wash parameters. Select a 2-6 second submerged dwell time for adequate pin washing. Click "next".
On the final screen select the number of slides loaded on each platen. A maximum of 10 slides can be loaded per platen.
Set the humidity to 60% to prevent sample evaporation and to avoid spot drying between depositions.
Use the Aushon 2470 arrayer software checklist to insure that the instrument/slides are ready to be printed and click "start".

When printing is complete, the software will prompt the user to either continue or quit. If additional slides are not being printed, select quit, save the run file, and close the software. Remove the microtiter plates and slides from the arrayer.

Turn the Aushon 2470 arrayer power off, and place the printed microarray slides in a slide box. Store the slide box in a plastic storage bag with desiccant at −20° C.

Immunostaining

Each array is probed with one antibody targeting the protein of interest. Commercially available or custom-made antibodies are compatible with the RPPA platform.

Reagents:
Reblot™ Mild Antigen Stripping solution 10× (Millipore/Chemicon)
Blocking solution: I-Block™ Protein Blocking Solution (Applied Biosystems)
Validated primary antibodies;
Biotinylated species-specific secondary antibody;
Dako Autostainer (Dako). This is optional, staining can be done manually;
Catalyzed Signal Amplification (CSA) kit (Dako);
Biotin blocking system (Dako);
Antibody diluent with background reducing components (Dako);
Phosphate Buffered Saline (PBS) 1× without calcium or magnesium supplemented with 1% BSA;
IRDye680 Streptavidin (Licor). The IRDye680 is a fluorescent dye with absorption and emission in the near infrared spectrum between 680 and 800 nm;
Tris Buffered Saline with Tween® (Dako).

RPPA Slide Pretreatment

RPPA slides with immobilized lysates are pre-treated and blocked prior to antibody staining. The slides are pretreated with Reblot™ solution, an antigen retrieval method, to enhance the signal:noise ratios to reduce background signal due to non-specific protein binding.

Allow frozen RPPA slides to warm at room temperature for approximately 5-10 minutes. Do not remove slides from the plastic bag containing desiccant until the slides have warmed slightly.

Prepare a 1× solution of Mild Reblot™ (stock is 10×) in dH$_2$O. Incubate the RPPA slides in 1× Mild Reblot™ solution for 15 minutes on a rocker/shaker. Use an adequate volume of Mild Reblot™ to cover the surface of the slides.

Decant the Reblot™ solution and wash the RPPA slides with 1×PBS (calcium and magnesium free) twice for 5 minutes each.

Decant the last PBS wash and immediately add blocking solution (I-Block solution) for a minimum of 60 minutes. Place slides with serum samples directly in I-Block solution.

Microarray Immunostaining

The sensitivity of the RPPA platform is significantly increased when the detection system is coupled with catalyzed signal amplification (CSA) chemistry. CSA methods are based on streptavidin-biotin mediated deposition of biotinylated tyramide as an amplification reagent (Agilent/DAKO). IRDye680 Streptavidin (LI-COR Biosciences) is used for fluorescent detection. A few advantages of the fluorescent method are high dynamic range in terms of signal detection (which allows avoiding long dilution curves) and high signal:noise ratio.

To quantify non-specific background signal generated from the interaction between the secondary antibody and the samples, it is essential to add a negative control slide stained with secondary antibody only. Antibodies from different animal species can be used during the same Autostainer run provided that a negative control slide is designated for each species of secondary antibody. The signal intensity of the slide probed with secondary antibody alone is subtracted from the signal intensity of the primary and secondary antibody stained slide during data analysis. Species of the primary antibodies used on the RPPA should be different than the species of the antibodies used for the Co-IP.

Select the unconjugated primary antibodies of interest. Select biotinylated secondary antibodies correlating to the species of the primary antibodies. Prepare CSA solutions according to the manufacturer's directions (See Baldelli et al Methods Mol Biol. 2017; 1606:149-169 for more details).

In brief the staining procedure requires:
Hydrogen peroxide, 3% (Ready to use, in the CSA kit);
Biotin Blocking System (Consists of two ready-to-use vials of Avidin and Biotin);
Protein block (Ready to use, in CSA kit);
Link antibody (Anti-mouse in CSA kit, other species must be purchased separately);
Streptavidin-biotin complex (in CSA kit). The streptavidin-biotin complex is prepared by combining three reagents labeled Streptavidin-biotin Complex Diluent, Streptavidin-biotin Complex, Reagent A, and Streptavidin-biotin Complex, Reagent B. Prepare the working reagent at least 30 minutes prior to use. Add one drop of reagent A and one drop of reagent B for every 1 ml of SABC diluent. Mix well.
Amplification reagent (Ready to use, in CSA kit).
IRDye680 Streptavidin to PBS supplemented with 1% BSA. Protect from light exposure.
Fill the buffer reservoir with 1× Tris Buffered Saline with Tween® (TBST) and the water carboy with dH$_2$O. Empty the waste container if necessary.
Load reagents and slides on the autostainer. Prevent the nitrocellulose from drying during slide loading. If necessary, rinse the slides with 1×TBST or I-block during the slide loading process.
Prime the water and the buffer pumps before starting the run.
Cover the autostainer. IRDye680 Streptavidin is a fluorescent dye. It is important to minimize IRDye680 Streptavidin and stained slide exposure to the light.
After the staining run concludes allow slides to air dry, remove the slides from the autostainer and protect the slides from light exposure.
Label the microarray slides specifying the date, study, and antibody that has been used in the staining procedure.
Store the slides in the dark at room temperature.

Sypro Ruby Protein Blot Stain for Total Protein Determination

For more accurate results, each stained sample should be normalized to its corresponding total protein concentration even if the protein concentration is estimated before microarrays are printed. Consistency in total protein concentration of the printed lysates reduces analytical variability between samples. It is highly recommended to print samples at a similar protein concentration across a microarray. Sypro Ruby is a fluorescent dye used to quantify the amount of protein present in each individual array spot. It has a sensitivity of 1.0 ng to 1.0 µg protein.

Reagents:
Sypro Ruby Protein Blot Stain (Invitrogen);
Fixative solution: 41.5 mL dH$_2$O, 3.5 mL Acetic Acid (final concentration 7% v/v), and 5.0 mL Methanol (final concentration 10% v/v). Store tightly closed at room temperature. Stable for 2 months; dH$_2$O;

Sypro Ruby Protein Blot StainingSelect the number of RPPA slides to be stained with Sypro Ruby.

Allow RPPA slide(s) to reach room temperature if the slides were stored at −20° C. This usually takes 5-10 minutes.

Wash slide(s) in dH$_2$O for 5 minutes with constant rocking.

Incubate slide(s), on a rotator at low speed, for 15 minutes with fixative solution. Use an adequate volume of fixative to cover the surface of the slides.

Discard the fixative solution and wash slides with dH$_2$O 4 times for 5 minutes.

Incubate slide(s) with Sypro Ruby Blot stain solution for 30 minutes. Protect slides from light during staining.

Rinse slides twice with dH$_2$O.

Air dry the array in an area protected from light, such as a drawer or cupboard.

Proceed to image detection with a fluorescent imaging system of choice.

RPPA slide scanning: Fluorescence image acquisition and data analysis

Antibody and Sypro Ruby Stained slides can be scanned using a fluorescent image capturing system such as a laser scanner.

Materials:

Fluorescent image capturing system such as a laser scanner;

Adobe® Photoshop software;

Analysis software such as MicroVigene™ (Vigene Tech), ArrayCAM® (Grace Bio-Labs) or ImageQuant (GE Healthcare).

Image acquisition and data analysis

Place the RPPA slides in a laser scanner.

Determine exposure time for each primary antibody slide. All Sypro Ruby stained slides from a print run need to be exposed with the same settings and for the same amount of time.

Scan each slide at a resolution of 10 µm.

Save the image as a TIFF file.

Scan the negative control (secondary antibody alone) so that the exposure time matches the one at which the antibody slides were collected (multiple acquisitions will be required).

Adjust the image appearance (inverted/not inverted; rotation etc.) as required by the image analysis software. Proceed with data analysis. TIFF images that are generated by the scanner can be imported to a variety of data analysis software programs including MicroVigene (Vigene Tech) or ImageQuant (GE Healthcare). Data analysis produces a single pixel intensity value for each array spot that is proportional to the amount of measured analyte. For each spot on the array, final intensity values generated by the analysis software are obtained after negative control (secondary antibody alone) subtraction and normalization to total protein. Once the corrected, normalized intensity values of each sample have been calculated, statistical analyses can be performed and data can be displayed using graphing programs or hierarchical clustering procedures.

Example 2

By isolation of protein complexes obtained from individual patient tissue sample, for example, one skilled in the art could obtain formalin fixed paraffin embedded tumor tissue samples from non-small cell lung cancer (NSCLC) patients via a core needle biopsy. The block is then sectioned into 8 micron sections on uncharged glass slides and lightly stained with hematoxylin and enriched tumor epithelium cells are procured by laser capture micro dissection under direct microscopic visualization. The captured tumor epithelium from each NSCLC patient sample are individually lysed in a non-denaturing detergent buffer to retain the in vivo assembled heterotypic complexes. The lysate is then processed by the Multinodal Protein Interactome Network Array methodology by first co-immunoprecipitation via an anti-EGFR antibody to capture EGFR along with associated proteins that have formed in vivo in the patient tumor. The EGFR co-IP is then printed on 4 nitrocellulose slides via reverse phase protein array. Each slide is then overplayed with a specific and different phospho-specific antibody:

Slide 1 phosphorylated EGFR (Y1173)
Slide 2 phosphorylated SHC (Y317)
Slide 3 phosphorylated HER3 (Y1279)
Slide 4 phosphorylated AKT (S473)

Lysates are scored using defined pre-defined outpoints to determine degree of pathway engagement and signaling in order to determine which patient has EGFR drug target activation. NSCLC patients whose tumors are found to have EGFR drug target activation are then treated with an appropriate EGFR inhibitor such as erlotinib.

Activation (phosphorylation) of the EGFR receptor along with physical association of adapter proteins such as SHC, IRS1 and other downstream signaling molecules allows for the identification of patients whose tumors are driven by this specific signaling network and that can benefit from treatment with a compound inhibiting EGFR activation, namely, erlotinib.

Example 3

Targeting transcription factors is extremely challenging in oncology. However, inhibition and stabilization of transcription factors in protein complexes represents a novel strategy for targeting cancer cells and developing novel therapeutic strategies. For example, in patients with wild-type p53 its interaction with the binding partner MDM2 leads to the degradation of the transcription factor p53 and the down-regulation of its activity. Identifying and targeting these interactions in tumors driven by these specific PPI led to the discovery of novel targetable mechanisms.

The embodiments describe a new approach to identifying protein-protein interactions in any cell type.

The embodiments further describe a new approach to treating a patient based on identifying protein-protein interactions in any cell type.

Other embodiments are also within the scope of the following claims.

In the claims, the terms "a" and "an" mean "one or more." Also, all references disclosed in the application are incorporated by herein in their entirety.

What is claimed is:

1. A method of treatment, comprising: obtaining a tissue sample from a patient, generating a lysate from the tissue sample, performing a protein complex immunoprecipitation by attaching a first antibody to the lysate to obtain a protein complex immunoprecipitate, performing a reverse phase protein array on the protein complex immunoprecipitate using a second antibody and a third antibody, identifying a protein complex, determining whether the protein complex comprises a known protein drug target, and treating the patient with a drug that interacts with the known protein drug target; wherein the first antibody used for immunoprecipitation is different from the second antibody and the third antibody used for the reverse phase protein array.

2. The method of treatment of claim 1, wherein the known protein drug target comprises EGFR and the drug comprises an EGFR inhibitor.

3. The method of treatment of claim 1, further comprising treating the patient with a therapeutic agent and monitoring a response of the patient to the treatment of the patient with the drug that interacts with the known protein drug target, wherein the known protein drug target is physically associating with other proteins known to transduce cellular signals and/or the drug disrupts a kinase activity or a protein-protein interaction.

4. The method of treatment of claim 1, wherein the tissue sample is derived from a diseased cell of the patient wherein the diseased cell is obtained from a tumor, blood, blood cells, fat, liver, nerve cells, saliva, urine, tears, vitreous fluid, brachial lavage, sputum, brain tissues, stromal tissue.

5. The method of treatment of claim 2, wherein the EGFR inhibitor comprises erlotinib.

6. The method of treatment of claim 1, wherein the tissue sample comprises mammalian cells.

7. The method of treatment of claim 1, further comprising treating the tissue sample with an agent prior to the performing the protein complex immunoprecipitation to obtain the lysate.

8. The method of treatment of claim 7, further comprising immunoprecipitating the lysate with one or more antibodies.

9. The method of treatment of claim 1, wherein the protein complex immunoprecipitation comprises an immunoprecipitating protein complex including EGFR, RAS, ERK, CREB, STAT, and/or AKT.

10. The method of treatment of claim 9, wherein the immunoprecipitating protein complex comprises EGFR.

11. The method of treatment of claim 1, wherein the performing the reverse phase protein array comprises using a robotic printing platform.

12. The method of treatment of claim 1, wherein the identifying the protein complex further comprises identification of an activated member of the protein complex.

13. The method of treatment of claim 12, wherein the activated member of the protein complex includes proteins that are phosphorylated, acylated, alkylated, hydroxylated, glycosylated, cleaved, iodinated, succinylated, amidated, myristoylated, farnysilated, and/or palmitoylated.

14. The method of treatment of claim 1, wherein the protein complex comprises a protein signaling complex.

15. The method of treatment of claim 1, further comprising identifying activated members of protein complexes which are drug targets of one or more of EGFR, RAS, ERK, CREB, STAT, and/or AKT-mTOR pathways.

16. The method of treatment of claim 1, wherein the known protein drug target is physically associating with other proteins known to transduce cellular signals.

17. The method of treatment of claim 1, wherein the drug disrupts kinase activity or protein-protein interaction.

18. The method of treatment of claim 1, wherein the tissue sample is from a non-small cell lung cancer (NSCLC) patient.

19. The method of treatment of claim 1, wherein determination of the protein drug target comprises comparative analysis of a multinodal protein interactome network of the tissue sample comprising a mutant vs. a wild type form of said mutant.

20. The method of treatment of claim 3, wherein the other proteins comprise an adapter protein comprising SHC or IRS1 or downstream proteins thereof.

* * * * *